United States Patent
Shi et al.

(10) Patent No.: US 11,562,806 B2
(45) Date of Patent: Jan. 24, 2023

(54) DRUG CRYSTAL STRUCTURE LANDSCAPE ANALYSIS SYSTEM AND LANDSCAPE ANALYSIS METHOD THEREOF

(71) Applicant: SHENZHEN JINGTAI TECHNOLOGY CO., LTD., Guangdong (CN)

(72) Inventors: Xuekun Shi, Guangdong (CN); Yongpan Chen, Guangdong (CN); Yang Liu, Guangdong (CN); Peiyu Zhang, Guangdong (CN); Jian Ma, Guangdong (CN); Lipeng Lai, Guangdong (CN); Shuhao Wen, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 902 days.

(21) Appl. No.: 16/466,040

(22) PCT Filed: May 9, 2018

(86) PCT No.: PCT/CN2018/086194
§ 371 (c)(1),
(2) Date: Jun. 3, 2019

(87) PCT Pub. No.: WO2019/134318
PCT Pub. Date: Jul. 11, 2019

(65) Prior Publication Data
US 2021/0265022 A1     Aug. 26, 2021

(51) Int. Cl.
*G16C 20/20*     (2019.01)
*G16C 20/90*     (2019.01)
*G06F 30/20*     (2020.01)
(Continued)

(52) U.S. Cl.
CPC ............. *G16C 20/20* (2019.02); *G06F 30/20* (2020.01); *G16C 20/90* (2019.02); *G06F 2111/02* (2020.01); *H04L 67/12* (2013.01)

(58) Field of Classification Search
CPC ........ G16C 20/20; G16C 20/90; G16C 20/80; G16C 20/60; G16C 20/64; G06F 30/20;
(Continued)

(56) References Cited

U.S. PATENT DOCUMENTS

| | | | |
|---|---|---|---|
| 10,556,934 B2 * | 2/2020 | Yonath | C07D 211/54 |
| 2002/0034774 A1 * | 3/2002 | Hultgren | A61K 31/7004 536/116 |
| 2003/0190670 A1 * | 10/2003 | Bursavich | G16B 15/30 435/7.1 |
| 2010/0023473 A1 | 1/2010 | Neumann | |

(Continued)

FOREIGN PATENT DOCUMENTS

| | | | | |
|---|---|---|---|---|
| CN | 101928045 A | * | 12/2010 | A61P 9/02 |
| CN | 102159230 A | * | 8/2011 | A61P 37/04 |

(Continued)

OTHER PUBLICATIONS

Price et al., "Can computed crystal energy landscapes help understand pharmaceutical solids?", Apr. 2016.*

(Continued)

*Primary Examiner* — Kandasamy Thangavelu
(74) *Attorney, Agent, or Firm* — Muncy, Geissler, Olds & Lowe, P.C.

(57) ABSTRACT

The invention belongs to the technical field of drug crystal analysis, and particularly relates to a drug crystal structure landscape analysis system and a landscape analysis method thereof. The drug crystal structure landscape analysis system calls a cloud computing interface to calculate the energy of input crystals through an algorithm deployed in the cloud in advance, and an energy-density space group landscape array (Continued)

diagram of the crystals is generated according to the computation results returned; and analysis is selectively carried out as needed, result reports arc analyzed and summarized as a final report, and the final report is converted into a text document. The drug crystal structure landscape analysis system and the landscape analysis method thereof satisfy the drug crystal structure analysis requirements in the new technology background, and can analyze a large quantity of crystals which are formed by a certain drug molecule and have different structures.

9 Claims, 8 Drawing Sheets

(51) Int. Cl.
*G06F 111/02* (2020.01)
*H04L 67/12* (2022.01)

(58) Field of Classification Search
CPC ...... G06F 2111/02; H04L 67/12; H04L 67/10; H04L 67/565; A61P 37/04; A61P 35/02; A61P 9/02; G16B 15/30; G16B 15/00
See application file for complete search history.

(56) References Cited

U.S. PATENT DOCUMENTS

2017/0032078 A1* 2/2017 Stelzer .................. G16C 20/60
2021/0375402 A1* 12/2021 Jin ........................ G16C 20/30

FOREIGN PATENT DOCUMENTS

CN      102770447 A  *  11/2012  ............. A61P 35/02
CN      106133734 A  *  11/2016  ............. G16B 15/00
WO   WO 2017015187 A1  *  1/2017  ............. G16C 20/64

OTHER PUBLICATIONS

Stelzer et al., U.S. Patent Application Publication 2017/0032078, Feb. 2017, see the short version.*
Bursavich et al., U.S. Patent Application Publication 2003/0190670, Oct. 2003, see the short version.*
Bhardwaj, R.M., "Exploring the Crystal Structure Landscape of Olanzapine", Feb. 2016.*
Blundel et al., "Quantification of free ligand conformational preferences by NMR and their relationship to the bioactive conformation" , Sep. 2013.*
Dubey, Ritesh et al.., "Crystal landscape in the orcinol:4,4'-bipyridine system: synthon modularity, polymorphism and transferability of multipole charge density parameters", Oct. 2013.*
"International Search Report (Form PCT/ISA/210) of PCT/CN2018/086194," dated May 9, 2018, pp. 1-4.
Luca Iuzzolino et al., "Use of crystal structure informatics for defining the conformational space needed for predicting crystal structures of pharmaceutical molecules," Journal of Chemical Theory and Computation, vol. 13, Issue 10, Sep. 11, 2017, pp. 1-32.
Sarah L. Price, "Predicting crystal structures organic compounds," Chem. Soc. Rev., vol. 43, Issue 7, Apr. 2014, pp. 2098-2111.

* cited by examiner

DRUG CRYSTAL STRUCTURE LANDSCAPE ANALYSIS SYSTEM AND LANDSCAPE ANALYSIS METHOD THEREOF

CROSS-REFERENCE TO RELATED APPLICATION

This application is a 371 of international application of PCT application serial no. PCT/CN2018/086194, filed on May 9, 2018. The entirety of the above-mentioned patent application is hereby incorporated by reference herein and made a part of this specification.

BACKGROUND OF THE INVENTION

1. Technical Field

The invention belongs to the technical field of drug crystal analysis, and particularly relates to a drug crystal structure landscape analysis system and a landscape analysis method thereof.

2. Description of Related Art

In traditional drug crystallographic studies, the crystal structure of drugs usually needs to be observed and analyzed and be extended according to settings to study the space group distribution of the molecules in cells. Sometimes, the hydrogen bonding and non-bonding effects in crystals also need to be analyzed to compare the structural similarities of different crystals.

For example, the most typical crystal analysis system, Mercury, mainly includes the following.

1. A module used for basic display of 3D structures of crystals.
2. A module used for editing the molecular structures of crystal structures.
3. A module used for analyzing the hydrogen bonding and non-bonding effects.
4. A module used for structural comparison of the crystals.

Generally, Mercury fulfills basic observation and analysis of crystals and satisfies the basic requirements of drug crystal scientists.

With the development of the Internet and cloud computing technologies, cloud computing resources have become available for scientific computation, and the crystal structure prediction technology has come into being accordingly. As the crystal structure prediction technology can predict, by quantum chemistry computation, all crystals possibly formed by drug molecules, one drug molecule may have a large quantity of different crystals which are to be analyzed by scientists.

Traditional drug crystal structure analysis systems cannot realize unified analysis of a large quantity of crystal structures of one molecule and thus cannot satisfy the requirements of novel crystal structure prediction technologies.

In addition, with the emergence of these possible crystal structures, superiority comparison of these structures becomes an issue to be settled. The traditional crystal structure analysis systems only realize structure comparison of crystals, but cannot realize superiority comparison of these crystals by certain indexes, and consequentially, the crystal sorting efficiency is extremely low in this case.

Particularly, in a scene where a large quantity of crystals needs to be analyzed, how to output analysis results is also an issue to be settled. If analysis results cannot be recoded and displayed for users, the work efficiency of the users will be reduced undoubtedly. In this aspect, traditional crystal structure analysis systems cannot output a systematic analysis result document after analyzing crystals and particularly a large quantity of crystals, which brings inconvenience to users and results in a poor user experience.

BRIEF SUMMARY OF THE INVENTION

In order to settle the above issues, the invention provides a drug crystal structure landscape analysis system and an analysis method thereof to satisfy the drug crystal structure analysis requirements in the new technology background. By adoption of the system and method, a large quantity of crystals which are formed by a certain drug molecule and have different structures can be analyzed, and the properties and similarities of the crystal structures can be analyzed in more aspects, so that more powerful analysis support is provided for users.

The specific technical solution adopted by the invention is as follows.

The drug crystal structure landscape analysis system mainly includes a drug crystal structure analysis basic module, a drug crystal structure landscape analysis module, and a cloud computing application programming interface (API) connected with a cloud computing structure, wherein:

The drug crystal structure analysis basic module includes a crystal 3D View module, a structure edit module, a hydrogen bonding and non-bonding effect module, and a structure comparison module, which is used for basic drug crystal structures analysis and provides basic support for drug crystal structure landscape analysis module.

The drug crystal structure landscape analysis module includes an experimental structure analysis module, a torsional conformation analysis module, a computation result landscape display module, which is capable of satisfying the analysis requirement of a large quantity of crystal structures by a landscape analysis mode and visually displaying drug crystal structure analysis results.

The cloud computing application programming interface (API) is used as a channel for the landscape analysis system to access to cloud computing resources and calculates the energy ranking and free energy data of the drug crystal structures by cloud computing, to provide external computing support for the drug crystal structure landscape analysis module.

The landscape analysis method of the drug crystal structure landscape analysis system includes the following process.

Call, by the drug crystal structure landscape analysis system, a cloud computing interface to calculate the energy of input crystals through an algorithm deployed in the cloud in advance; generate an energy-density space group landscape array diagram of the crystals according to the computation results returned; selectively carry out the following five analyses as needed.

(1) Similarity analysis of space groups and structures of the crystals.

Particularly, the space group information of the crystals is compared with the positions of molecules in cells to figure out similar crystals belonging to the same category, from output crystals; and then output a result report is.

(2) Analysis of hydrogen bonding and non-bonding effects of the crystals.

Particularly, bonding types of the hydrogen bonding or non-bonding effects of the crystals are analyzed to figure out crystal structures having similar hydrogen bonding or non-bonding effects, from the output crystals; and output a result report.

(3) Comparative analysis of experimental structures of the crystals.

Particularly, output crystal structures are compared with the experimental structures to figure out crystal structures which are most similar to the experimental structures, X-ray diffraction (XRD) spectrums of the crystal structures, and the experimental structures are compared to verify the validity of prediction results, and output a result report.

(4) Torsional conformation analysis of molecules in the crystals.

Particularly, torsional angles of the molecules are scanned, and the probability of occurrence of conformations under different torsional angles is analyzed to obtain preferential conformations of the molecules, and then output a result report.

(5) Stability analysis of the crystals at different temperatures.

Particularly, the relation between the free energy of the crystals and the temperature is calculated, the cloud computing interface is called to use cloud computing resources, and after the crystals and computing parameters are input, variations of the free energy of the crystals with temperature are returned; and an result report is output and displayed as a variation curve of the free energy of the crystals with temperature.

The above analysis result reports are summarized as a final report, and the final report is converted into a text document.

The drug crystal structure landscape analysis method provided by the invention has the following technical effects.

1. A good contrastive analysis effect is fulfilled for a huge crystal structure set, represented by crystal structure prediction.

2. External algorithms can be called to satisfy various computing requirements.

3. Computation and analysis results can be displayed as interactive reports so as to be saved by users.

DETAILED DESCRIPTION OF THE INVENTION

The specific technical solution of the invention is explained below in combination with embodiments.

A landscape array diagram obtained after energy calculation visually shows the energy ranking sequence of all crystal structures. The crystal structure with the lowest energy is searched out from similar crystal structures through structure similarity analysis, and an experimental crystallization scheme of this crystal structure is obtained through hydrogen analysis of this structure. It is discovered by stability analysis that this crystal structure will not be converted into other structures when the temperature rises. Upon XRD detection, this crystal structure obtained through experiments is consistent with an actual structure, and this directly verifies the validity of the crystal structure prediction result.

Figure 1:
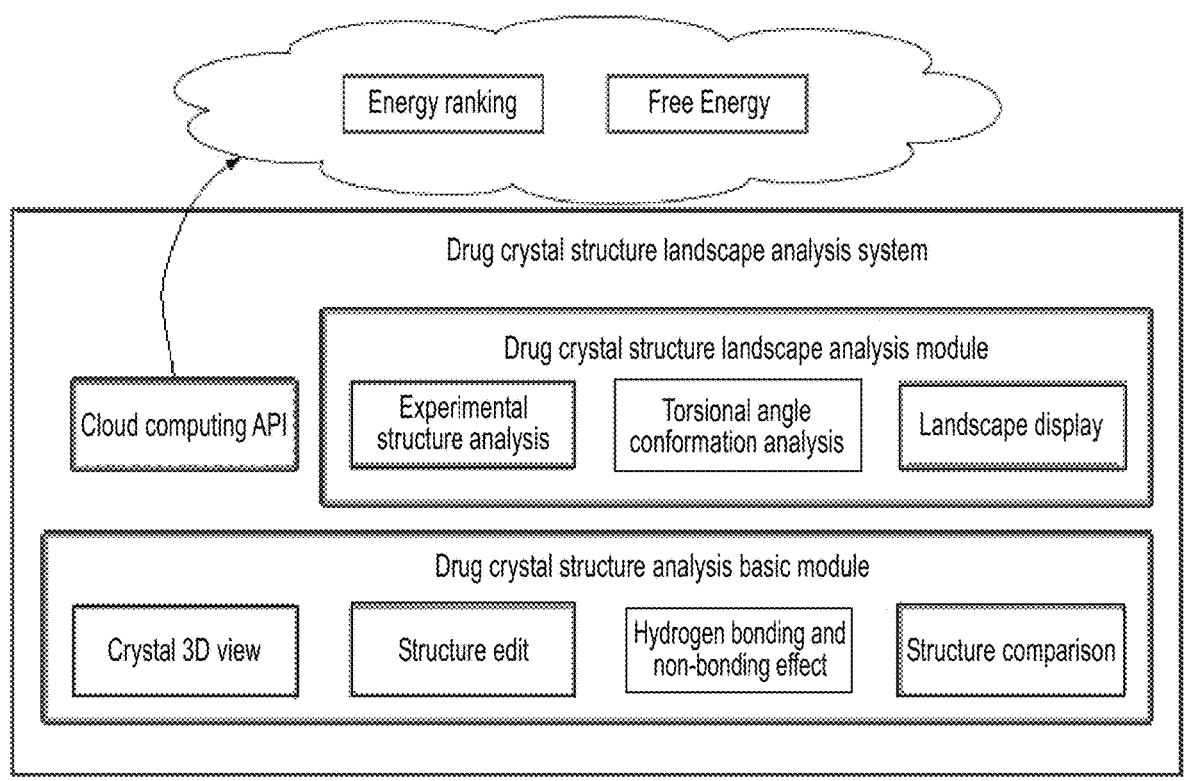
FIG. 1 is a schematic diagram of the system of the invention.

FIG. 1 is a functional diagram of the system.

The drug crystal structure landscape analysis system mainly consists of a drug crystal structure analysis basic module, a drug crystal structure landscape analysis module, and a cloud computing API connected with a cloud computing structure.

The drug crystal structure analysis basic module has a crystal 3D View function, a structure edit function, a hydrogen bonding and non-bonding effect function, a structure comparison function, and other conventional functions, thereby satisfying the basic analysis requirement of drug crystal structures and providing basic support for advanced functions of the landscape analysis module.

The drug crystal structure landscape analysis module is the core module of the whole system, has an experimental structure analysis function, a torsional conformation analysis function, a computation result landscape display function, and the like, which is capable of satisfying the analysis requirement of a large quantity of crystal structures by a landscape analysis mode and capable of generating results more visually, compared with traditional drug crystal structure analysis methods.

The cloud computing API provides a channel for the landscape analysis system to access to cloud computing resources. Energy ranking and free energy data, which are necessary for routine landscape analysis and require large computation, of the drug crystal structures are acquired by cloud computing, so that external computing support is provided for the landscape analysis module.

Figure 2:
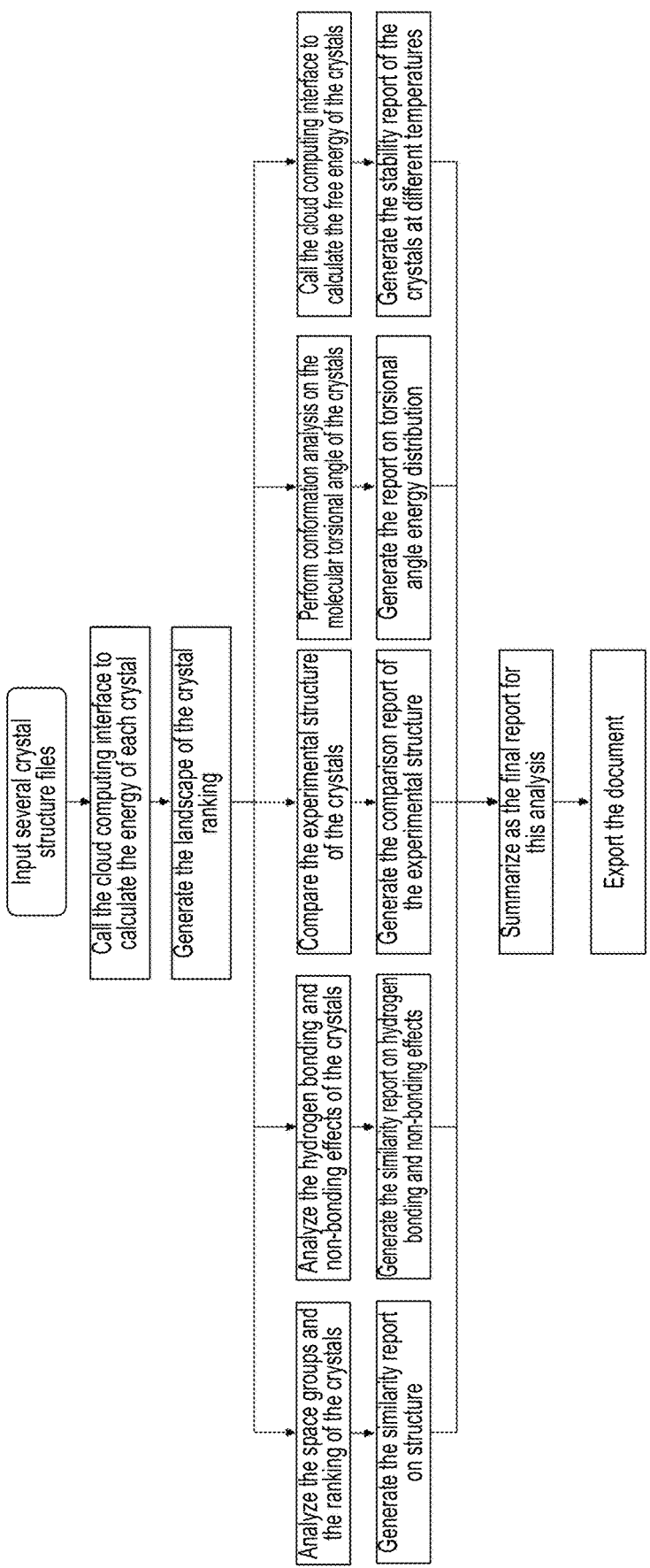
FIG. 2 is a flow diagram of the invention.

FIG. 2 shows a specific usage process and corresponding functional modules.

Figure 3:
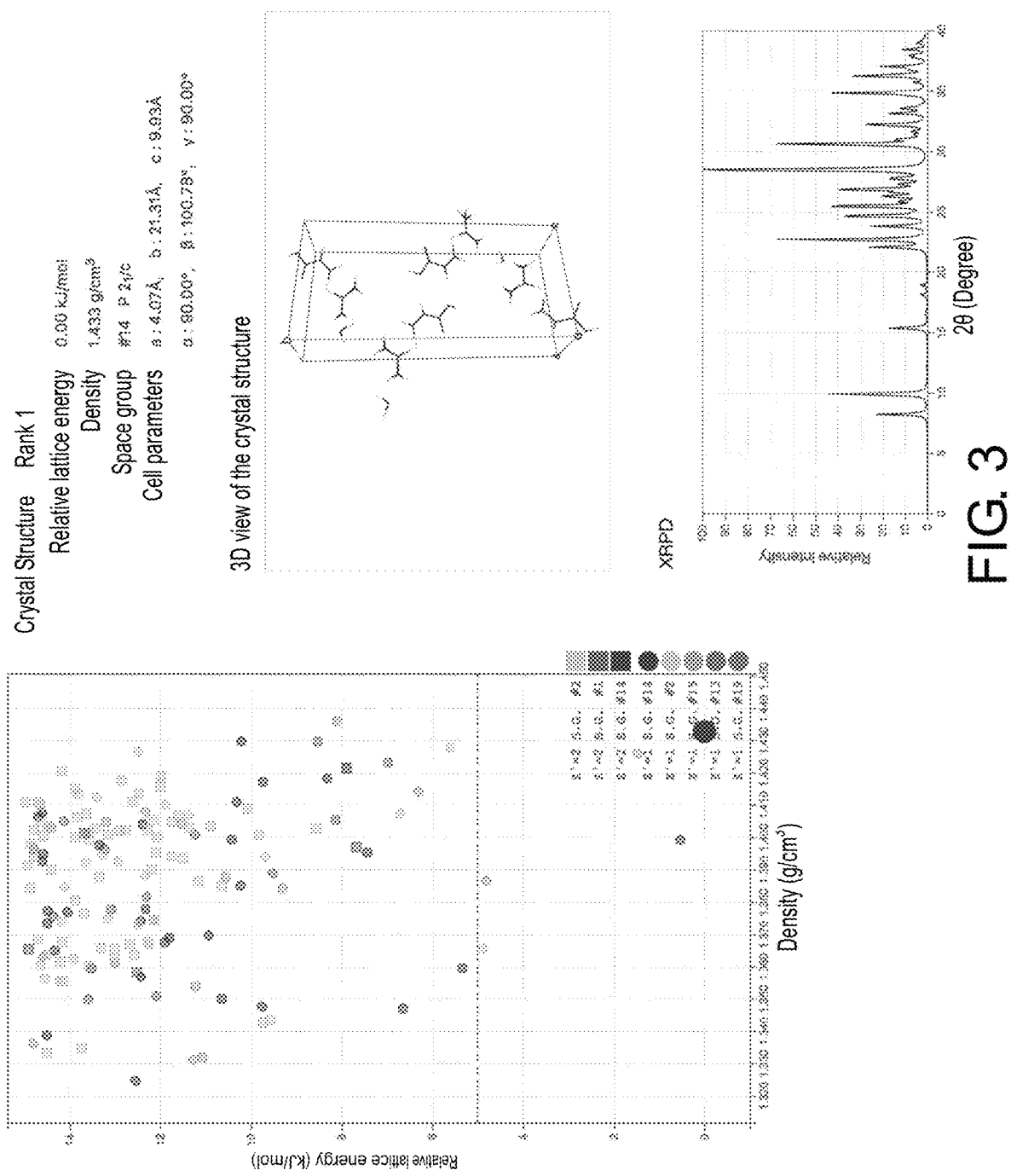
FIG. 3 is a landscape array diagram of an embodiment.

With the crystal structure prediction as an example, a large quantity of crystal structures is generated and compared with certain known experimental structures. The drug crystal structure landscape analysis system calls a cloud computing interface to calculate the energy of crystals through an algorithm deployed in the cloud in advance, such as quantum chemical methods or force field methods; and an energy-density space group landscape array diagram of the crystals is generated according to the computation results returned, as shown in FIG. 3. This diagram shows the energy relation of all the input crystals, and the crystal structure with lower energy is more stable.

After energy calculation, the following five analyses are selectively carried out as needed.

(1) Similarity analysis of space groups and structures of the crystals.

Figure 4:
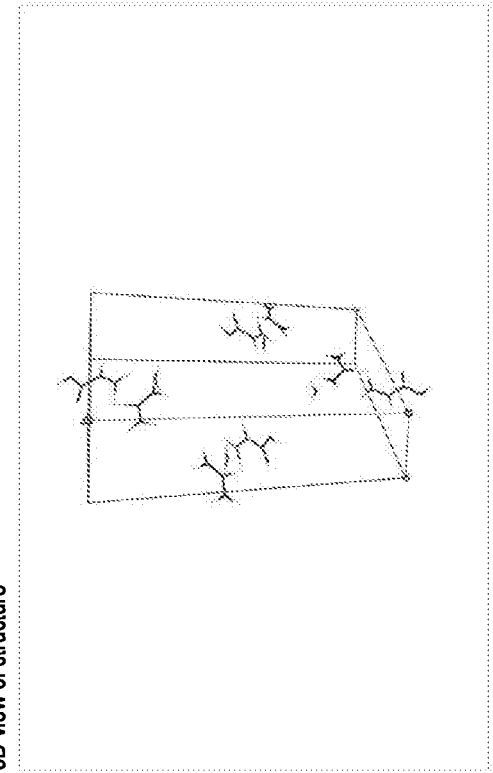
FIG. 4 is a result report of similarity analysis of space groups and structures of crystals in the embodiment.
Figure 4:
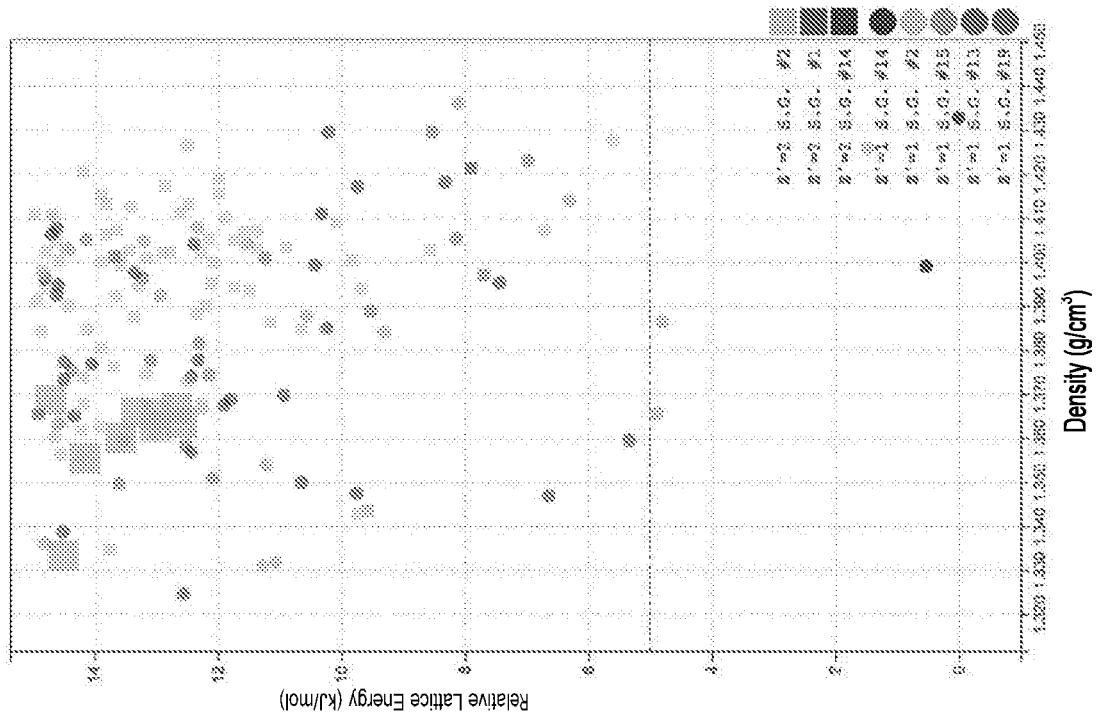

The space group information of the crystals can be compared with the positions of molecules in cells to figure out similar crystals belonging to the same category, from output crystals. An analysis result shows preferential structures of the crystals. A structure having the lowest energy will be formed by crystals with similar structures during crystallization. An output result report is shown in FIG. 4.

(2) Analysis of hydrogen bonding and non-bonding effects of the crystals.

Figure 5:
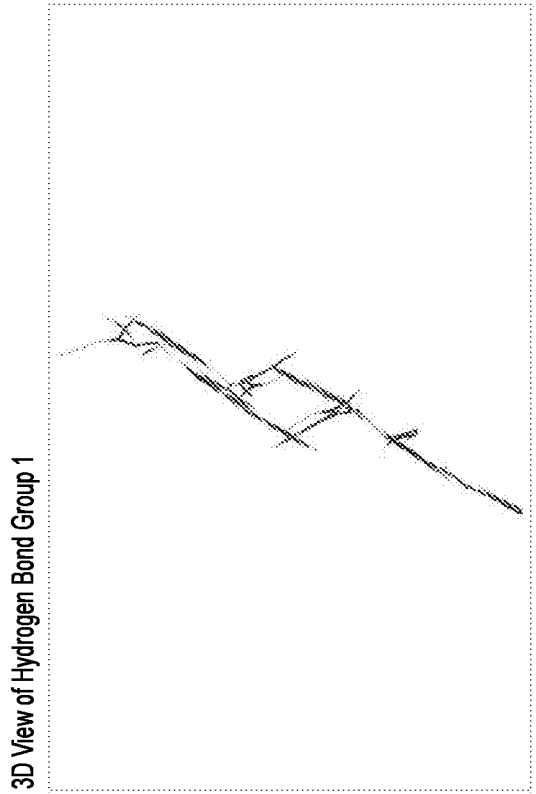
FIG. 5 is a result report of an analysis of hydrogen bonding and non-bonding effects of the crystals in the embodiment.
Figure 5:
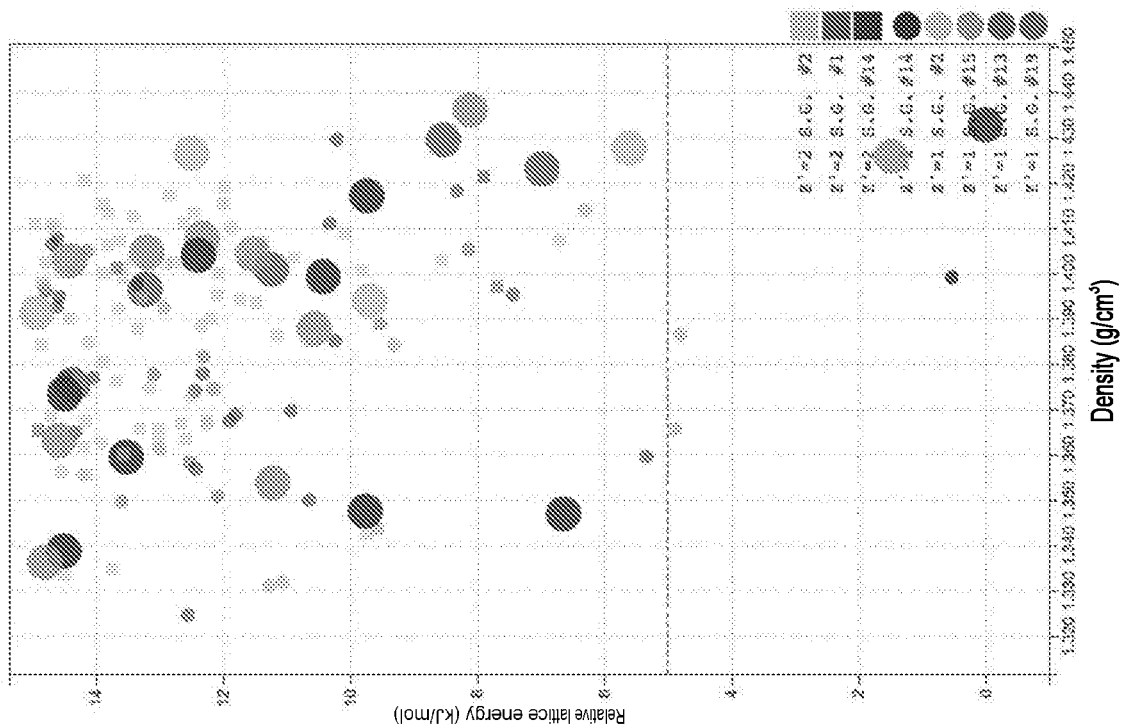

Hydrogen bonding effects or certain strong non-bonding effects have a great influence on the overlapping of molecules in cells and thus are crucial crystal analysis elements. Bonding types of the hydrogen bonding or non-bonding effects of the crystals can be analyzed to figure out crystal structures having similar hydrogen bonding or non-bonding effects, from the output crystals. Crystals containing certain hydrogen bonds can be induced to be crystallized in experiments, thereby having a guidance effect on the experiments. An output result report is shown in FIG. 5.

(3) Comparative analysis of experimental structures of the crystals.

Figure 6:
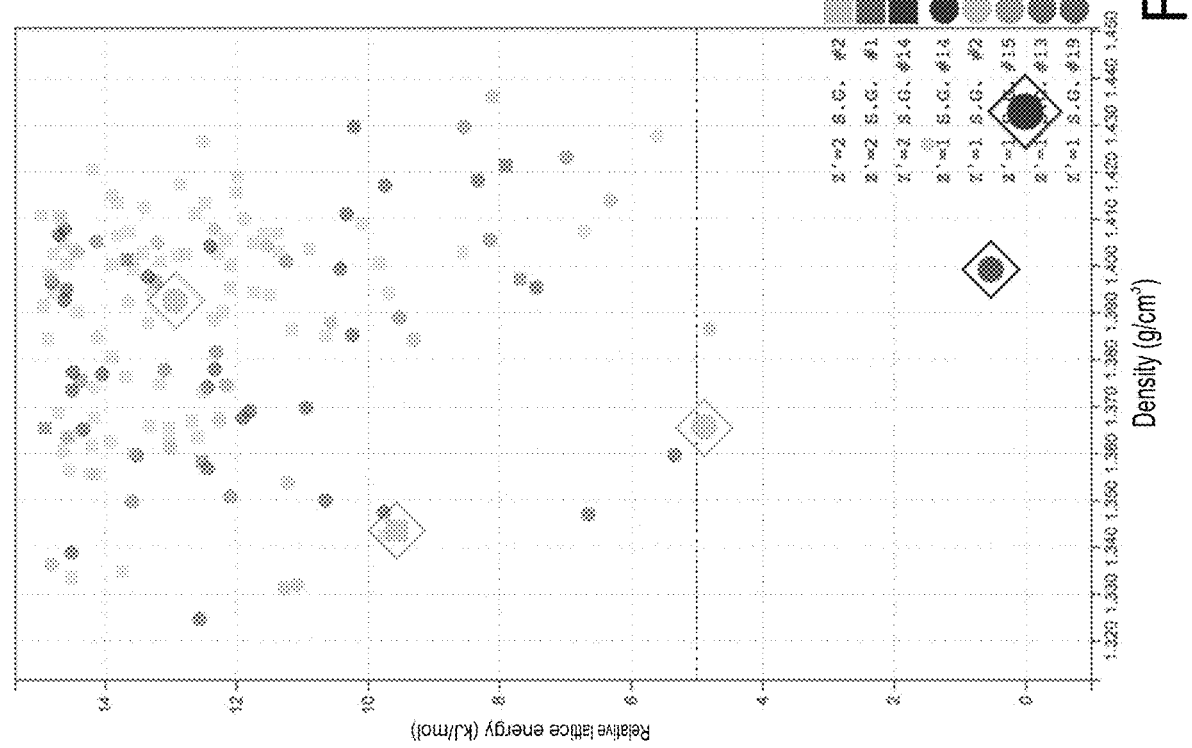
FIG. 6 is a result report of a comparative analysis of experimental structures of the crystals in the embodiment.
Figure 6:
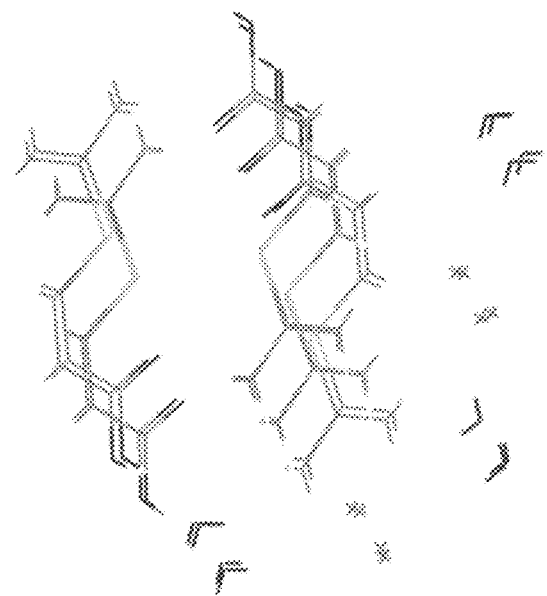
Figure 6:
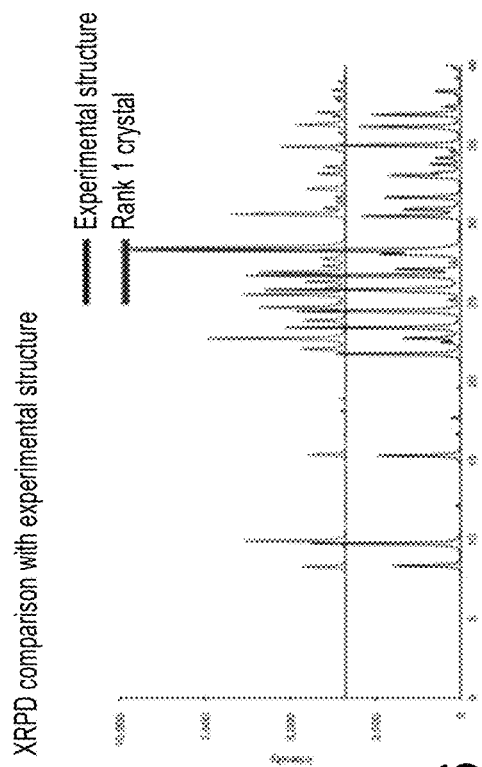

As for crystal structure prediction, the experimental structures of the crystals of corresponding molecules can verify the prediction validity. To fulfill this function, output crystal structures can be compared with the experimental structures to figure out crystal structures which are most similar to the experimental structures, and XRD spectrums of the crystal structures and the experimental structures are compared to verify the validity of prediction results. An output result report is shown in FIG. 6.

(4) Torsional conformation analysis of molecules in the crystals.

Figure 7:
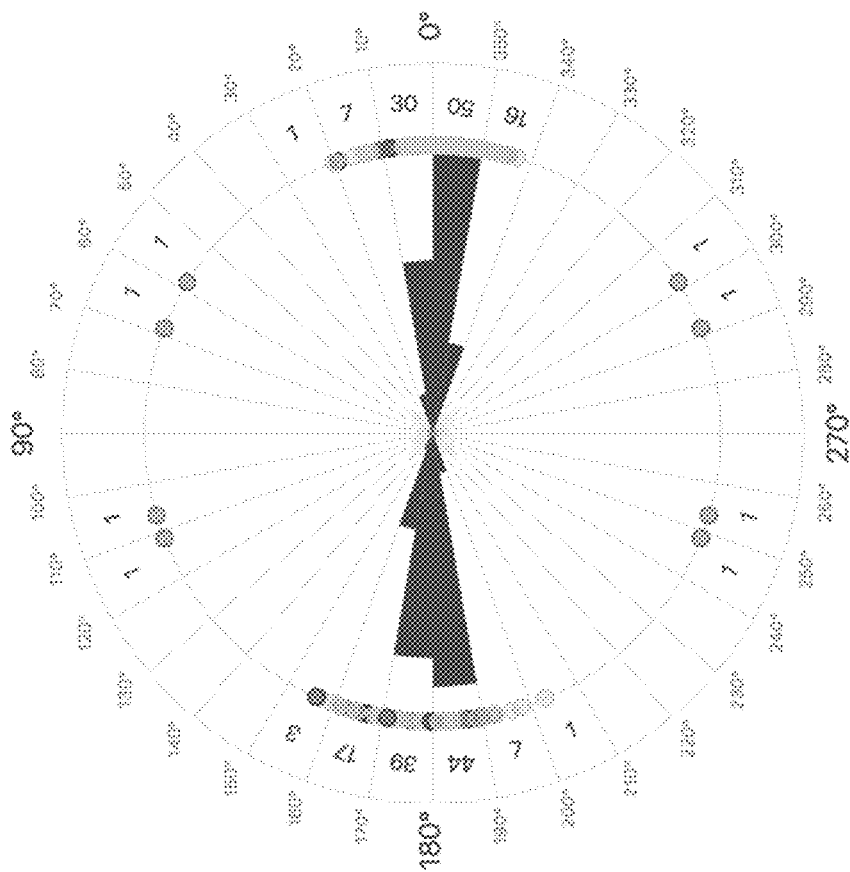
FIG. 7 is a result report of a torsional conformation analysis of molecules in the crystals in the embodiment.
Figure 7:
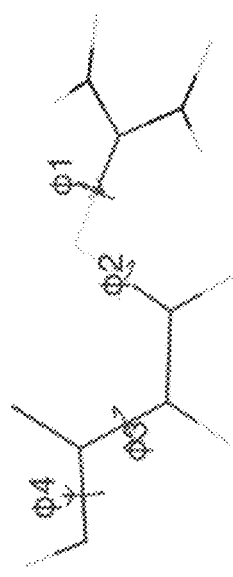

As for molecules constituting the crystals, different molecule conformations have an influence on the overlaying mode of the molecules in the cells. The landscape analysis system can scan the torsional angles of the molecules and analyze the probability of occurrence of the conformations under different torsional angles so as to obtain preferential conformations of the molecules, an output result report is shown in FIG. 7.

(5) Stability analysis of the crystals at different temperatures.

Figure 8:
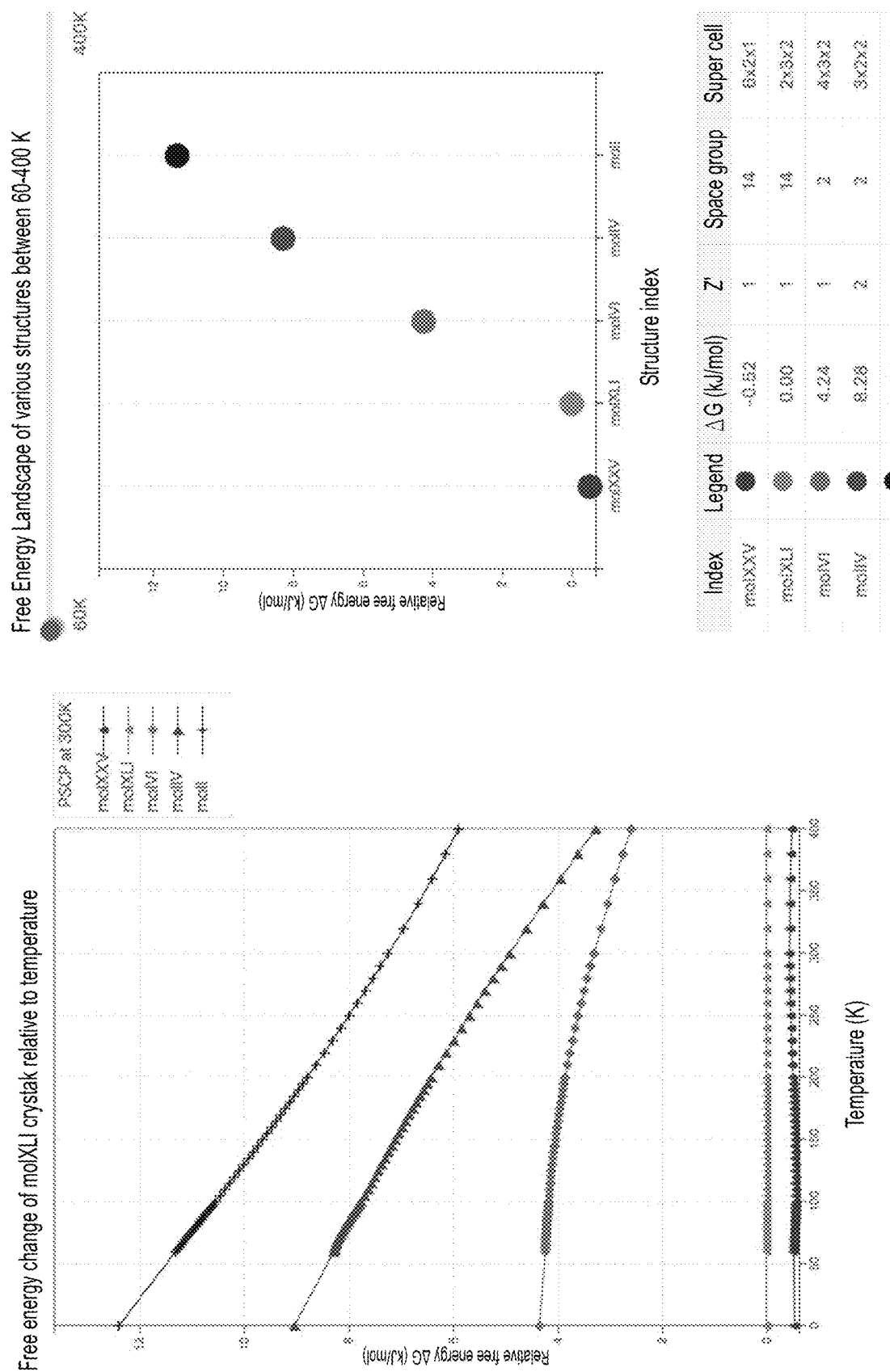
FIG. 8 is a result report of a stability analysis of the crystals at different temperatures in the embodiment.

Usually, the crystal structure prediction can only work out the energy of crystals at a certain temperature, while in actual application, the energy of the crystals will change with temperature variations, which in turn causes crystal transformations. In this case, the relation between the free energy of the crystals and the temperature needs to be calculated. It generally takes a long time to calculate the free energy. The cloud computing interface can be called to use cloud computing resources, and after the crystals and computing parameters are input, variations of the free energy of the crystals with temperature are returned. An analysis result will be displayed in the system as a variation curve of the free energy of the crystals with temperature, so that data can be analyzed by users to determine the variation of the stability of the crystals with temperature as well as the transformational relation between the crystals. An output result report is shown in FIG. 8.

All the above analysis results can be saved as interactive reports so as to be reviewed and analyzed by users and can also be converted into a text document in a PDF or word format to be exported.

What is claimed is:

1. A drug crystal structure landscape analysis system, including a drug crystal structure analysis basic module, a drug crystal structure landscape analysis module, and a cloud computing API connected with a cloud computing structure, wherein the drug crystal structure analysis basic module includes a crystal 3D View module, a structure edit module, a hydrogen bonding and non-bonding effect module, and a structure comparison module, which is used for basic drug crystal structures analysis and provides basic support for the drug crystal structure landscape analysis module;

the drug crystal structure landscape analysis module includes an experimental structure analysis module, a torsional conformation analysis module and a computation result landscape display module, which is capable of satisfying an analysis requirements of a large quantity of crystal structures in a landscape analysis mode and visually displaying drug crystal structure analysis results and drug crystal structure landscape analysis results;

the cloud computing API is used as a channel for the landscape analysis system to access to cloud computing resources and calculates energy ranking and free energy data of the drug crystal structures by cloud computing, to provide external computing support for the drug crystal structure landscape analysis module, wherein a target crystal structure is determined based on an energy ranking of input crystal structures;

wherein the drug crystal structure analysis results visually displayed by the computation result landscape display module comprise a landscape array diagram including an energy-density space group landscape array diagram of the input crystal structures, a textbox showing values of given parameters of the target crystal structure, 3D view of the target crystal structure, and an X-ray diffraction (XRD) spectrum of the target crystal structure;

wherein the energy-density space group landscape array diagram visually shows the energy ranking of the input crystal structures.

2. A landscape analysis method of a drug crystal structure landscape analysis system, wherein the drug crystal structure landscape analysis system includes a drug crystal structure analysis basic module, a drug crystal structure landscape analysis module, and a cloud computing API connected with a cloud computing structure, wherein the drug crystal structure analysis basic module includes a crystal 3D View module, a structure edit module, a hydrogen bonding and non-bonding effect module, and a structure comparison module, which is used for basic drug crystal structures analysis and provides basic support for the drug crystal structure landscape analysis module;

the drug crystal structure landscape analysis module includes an experimental structure analysis module, a torsional conformation analysis module, a computation result landscape display module, which is capable of satisfying an analysis requirements of a large quantity of crystal structures in a landscape analysis mode and visually displaying drug crystal structure analysis results and drug crystal structure landscape analysis results;

the cloud computing API is used as a channel for the landscape analysis system to access to cloud computing resources and calculates energy ranking and free energy data of the drug crystal structures by cloud computing, to provide external computing support for the drug crystal structure landscape analysis module;

wherein the landscape analysis method comprises the following steps:

calling, by the drug crystal structure landscape analysis system, a cloud computing API to calculate energy of input crystal structures through an algorithm deployed in a cloud in advance;

generating an energy-density space group landscape array diagram of the input crystal structures according to computation results returned, wherein the energy-density space group landscape array diagram visually shows an energy ranking of the input crystal structures;

wherein a target crystal structure is determined based on the energy ranking of input crystal structures;

wherein the target crystal structure is identified as a crystal structure with a lowest energy in a group of similar crystal structures which are obtained based on comparing space group information of the input crystal structures with positions of molecules in cells;

wherein the drug crystal structure analysis results visually displayed by the computation result landscape display module comprise a landscape array diagram including an energy-density space group landscape array diagram of the input crystal structures, a textbox showing values of given parameters of the target crystal structure, 3D view of the target crystal structure, and an X-ray diffraction (XRD) spectrum of the target crystal structure;

carrying out selected analyses of the target crystal structure and generating result reports of the selected analyses;

analyzing the result reports, and summarizing the result reports as a final report; and converting the final report into a text document.

3. The landscape analysis method according to claim 2, wherein the analyses are selected from a group of analyses including:

(1) similarity analysis of space groups and structures of the crystals, wherein space group information of the crystals is compared with positions of molecules in cells to figure out similar crystals belonging to a same category, from output crystal structures; and then output a result report of the similarity analysis of the space groups and the structures of the crystals;

(2) analysis of the hydrogen bonding and non-bonding effects of the crystals, wherein bonding types of the hydrogen bonding or the non-bonding effects of the crystals are analyzed to figure out the crystal structures having similar hydrogen bonding or non-bonding effects, from the output crystal structures; and output a result report of the analysis of the hydrogen bonding and the non-bonding effects of the crystals;

(3) comparative analysis of experimental structures of the crystals, wherein the crystal structures are compared with the experimental crystal structures to figure out the crystal structures which are most similar to the experimental crystal structures, XRD spectrums of the crystal structures, and the experimental crystal structures are compared to verify a validity of prediction results, and output a result report of the comparative analysis of the experimental structures of the crystals;

(4) torsional conformation analysis of molecules in the crystals, wherein torsional angles of the molecules are scanned, and a probability of occurrence of conformations under different torsional angles is analyzed to obtain preferential conformations of the molecules, and then output a result report of the torsional conformation analysis of the molecules in the crystals;

(5) stability analysis of the crystals at different temperatures, wherein a relation between free energy of the crystals and a temperature is calculated, the cloud computing API is called to use the cloud computing resources, and after the crystals and computing parameters are input, variations of the free energy of the crystals with temperature are returned; and a result report of the stability analysis of the crystals at the different temperatures is output and displayed as a variation curve of the free energy of the crystals with temperature.

4. The landscape analysis method according to claim 3, wherein the result report of the similarity analysis of the space groups and the structures of the crystals includes the energy-density space group landscape array diagram, a table of similar packing groups, and 3D view of crystal structure.

5. The landscape analysis method according to claim 3, wherein the result report of the analysis of the hydrogen bonding and the non-bonding effects of the crystals includes the energy-density space group landscape array diagram, a table of similar hydrogen bond groups, 3D view of one of the similar hydrogen bond groups.

6. The landscape analysis method according to claim 3, wherein the result report of the comparative analysis of the experimental structures of the crystals includes the energy-density space group landscape array diagram, structure overlay between the target crystal structure and single crystal structure of the experimental crystal, and XRD comparison between the target crystal structure and the experimental crystal structure.

7. The landscape analysis method according to claim 3, wherein the result report of the torsional conformation analysis of the molecules in the crystals includes 3D view of the torsional angles and angular distribution of one of the torsional angles.

8. The landscape analysis method according to claim 3, wherein the result report of the stability analysis of the crystals at the different temperatures includes free energy landscape of various structure within a temperature range.

9. A method to verify validity of a predicted drug crystal structure, comprises:

inputting files of crystal structures;

calling a cloud computing API to calculate energy of each of the crystal structures;

generating a landscape array diagram that visually shows an energy ranking of all crystal structures based on the energy calculation;

identifying a target crystal structure with a lowest energy from similar crystal structures through structure similarity analysis;

outputting an experimental crystallization scheme of the target crystal structure through hydrogen bond analysis of the target crystal structure;

discovering whether the target crystal structure will be converted into other structures when the temperature rises through stability analysis of the target crystal structure;

obtaining an experimental crystal structure based on the experimental crystallization scheme; and comparing XRD spectrums of actual crystal structures and the experimental crystal structure;

visually displaying the landscape array diagram including an energy-density space group landscape array diagram of the input crystal structures, a textbox showing values of given parameters of the target crystal structure, 3D view of the target crystal structure, and an X-ray diffraction (XRD) spectrum of the target crystal structure.

\* \* \* \* \*